United States Patent [19]
Bracher

[11] Patent Number: 5,989,585
[45] Date of Patent: Nov. 23, 1999

[54] TRANSDERMAL THERAPEUTIC SYSTEM (TTS) CONTAINING VITAMIN E FOR THE TREATMENT OF DRUG DEPENDENCY

[75] Inventor: Daniel Bracher, Holzkirchen, Germany

[73] Assignee: Hexal AG, Holzkirchen, Germany

[21] Appl. No.: 09/051,845

[22] PCT Filed: Oct. 14, 1996

[86] PCT No.: PCT/EP96/04459

§ 371 Date: Jun. 23, 1998

§ 102(e) Date: Jun. 23, 1998

[87] PCT Pub. No.: WO97/15294

PCT Pub. Date: May 1, 1997

[30] Foreign Application Priority Data

Oct. 23, 1995 [DE] Germany .............. 195 39 373

[51] Int. Cl.⁶ .................................. A61F 13/02
[52] U.S. Cl. ................ 424/448; 424/447; 424/449; 514/458
[58] Field of Search ................. 424/447, 448, 424/449; 514/458

[56] References Cited

U.S. PATENT DOCUMENTS 5,683,711  11/1997  Fischer et al. ............... 424/449

FOREIGN PATENT DOCUMENTS

92/19226  11/1992  WIPO .
94/23707  10/1994  WIPO .

*Primary Examiner*—Gollamudi S. Kishore
*Assistant Examiner*—Lakshmi Channavajjala
*Attorney, Agent, or Firm*—Kane, Dalsimer, Sullivan and Levy, LLP

[57] ABSTRACT

The invention relates to a transdermal therapeutic system (TTS) for the administration of active agents for substitution treatment of drug dependency or drug addiction.

12 Claims, 1 Drawing Sheet

RELATIONSHIP BETWEEN FLUX AND AGENT
CONCENTRATION IN THE MATRIX FOR SKIN PERMEATION
IN VITRO THROUGH ISOLATED MOUSE SKIN.

TRANSDERMAL THERAPEUTIC SYSTEM (TTS) CONTAINING VITAMIN E FOR THE TREATMENT OF DRUG DEPENDENCY

FIELD OF INVENTION

The present invention relates to the transdermal administration of substances which are suited for substitution treatment of drug dependents and drug addicts, in particular to the structure of a transdermal therapeutic system (TTS) and a method for administration of such substances through intact skin. Concerning the suited substances, one could contemplate for example methadone, acetylmethadol, naltrexon, codeine or dihydrocodeine. In principle, the application of other strongly effective pain relievers is possible, for example morphine or buprenorphine. Methadone, mentioned as an example, is used in substitution therapy for opiate addicts, for example heroin addicts. One uses the L-enantiomorph as hydrochloride in the form of an aqueous solution, which is applied orally. The strongly analgesic effect of methadone is also used for drug dependent AIDS patients.

BACKGROUND OF INVENTION

Transdermal therapeutic systems for combating drug dependency and drug addiction are known, for example WO-A-9 219 226, WO-A-9 410 987, EP-B-0 113 562, EP-B-0 117 027 and EP-B-0 280 413.

The document WO-A-9 219 226 describes an application system containing lobeline for combating drug dependency. WO-A-9 410 987 relates to a combination of two application systems containing methadone. In EP-B-0 113 562, a container is suggested with which methadone can be applied through the skin. EP-B-0 117 027 describes a salve, a cream or a gel with an amount of methadone. Finally, a pharmaceutical composition is suggested in EP-B-0 280 413 for transdermal application of methadone with the aid of a permeation accelerator.

In principle, a transdermal administration of methadone and corresponding substances is preferable over an oral or parenteral application. It is apparent that a transdermal therapeutic system. (TTS) offers much greater security with respect to abusive use. For example, extraction of the drug from the TTS matrix without skilled knowledge is not possible. An abusive parenteral application by an addict to obtain satisfaction is much less of a danger than for example a solution administered orally.

A therapy using transdermal therapeutic systems can be carried out without direct supervision or without a doctor. A further advantage is the direct control of the dosage by means of the permeation surface. In withdrawal therapy, the necessary dosages can be adapted to the individual needs of the addict in simple manner. The known advantages of a transdermal application are also present, namely avoidance of the high dosage necessary for oral application, which accommodates the first-pass effect, and better control of the blood values.

The document DE-A4 339 400 describes a drug plaster in the form of a laminate, which includes a carrier and a matrix of a single polymer and an amount of vitamin E or a vitamin E derivative as well as at least one active agent, which can be an analgesic agent. The flux J of the active agent through a membrane of defined thickness, for example through the skin, should follow the equation:

J=diffusion coefficient D×diffusion surface A×distribution coefficient K×agent concentration on the donor side of the membrane $C_o$/membrane thickness h.

SUMMARY OF INVENTION

The agent flux J is thus proportional to the agent concentration $C_o$. However, if one would replace an oral application, for example of methadone, by a transdermal application and if one will avoid low molecular alcohols as permeation promoters, then (even apart from the first-pass effect) such a high agent concentration would be necessary that DE5-A4 339 400 could not offer a solution.

The object of the present invention is solved with a transdermal therapeutic system (TTS) for the administration of methadone in the form of a racemate (D,L-methadone) or one of its enantiomers, acetylmethadol in the form of its racemate (D,L-Acetylmethadol) or one of its enantiomers, naltrexon, codeine, dihydrocodeine, morphine, buprenorphine and/or one of their pharmaceutically acceptable salts as the active agent. The system for the treatment of drug dependency or drug addiction is provided with a self-adhesive layer-like matrix containing an amount of active agent or agents, where on or over one side of the matrix is provided a cover foil (backing liner) and on or over the other side of the matrix a release foil (release liner) is provided.

Further, the object of the present invention is solved by a transdermal therapeutic system (TTS) for the administration of methadone in the form of a racemate (D,L-methadone) or one of its enantiomers, acetylmethadol in the form of its racemate (D,L-acetylmethadol) or one of its enantiomers, naltrexon, codeine, dihydrocodeine, morphine, buprenorphine and/or one of their pharmaceutically acceptable salts as the active agent for the treatment of drug dependency or drug addiction. The system comprises an outer backing liner, a reservoir for the active agent, an adhesive element for skin contact of the plaster and a removable protection layer, where the reservoir, apart from the active agent, optionally includes permeation promoters, emulsifiers, thickening agents and/or common additives. According to Hadgraft & Wolff, Physicochemical and pharmacokinetic parameters affecting percutaneous absorption in Dermal and Transdermal-Drug Delivery, volume 31 (1993), pages 161, APV paperback, the diffusion law of Fick would be applicable for mass transport through homogeneous membranes such as the skin. The equation describes a linear relationship between the flux J and the concentration in the vehicle $C_o$ under steady state conditions.

$$J=KDA(C_o-C_s)/h=kp \text{ delta } C$$

| | |
|---|---|
| J | flux, for example in $\mu g/cm^2/h$ |
| K | distribution coefficient of the membrane (skin)/vehicle (dimensionless) |
| kp | permeability coefficient (cm/h) |
| D | diffusion coefficient in the membrane ($cm^2/s$) |
| A | permeation surface area($cm^2$) |
| h | membrane thickness (cm) |
| $C_v$ | concentration in the vehicle |
| $C_s$ | concentration in the membrane under sink conditions (i.e. continual transport of the agent from the membrane). |

In the experiments underlying the present invention, it was surprisingly found that for example with L-methadone as the agent, the amount of agent which permeates in an in vitro test with mouse skin did not increase linearly with the increase in agent concentration in the matrix, but was overproportional or greater than linear. This is surprising, because it could not be expected from the prior art that a transdermal therapeutic system, for example with L-methadone as the active agent, would deliver a permeation rate as high as that required for a rational transdermal therapy with amounts of 10 to 15 mg/day.

The active agents contemplated include for example methadone in the form of a racemate (D,L-methadone) or one of its enantiomers, acetylmethadol in the form of its racemate (D,L-acetylmethadol) or one of its enantiomers, naltrexon, codeine, dihydrocodeine, morphine, buprenorphine and/or one of their pharmaceutically acceptable salts. L-methadone is preferred.

The transdermal therapeutic system according to the present invention can be characterized by an amount of at least about 5, preferably about 10 and more preferably about 15 weight-% methadone based on the matrix or the reservoir of the plaster ready for application.

Particularly preferred is an amount of 15 to 20 weight-% methadone.

The transdermal therapeutic system according to the present invention can also be characterized by a matrix with an additional amount of vitamin E or a vitamin E derivative, optionally in the form of an oil-base solution, such as D-α-tocopherol.

The amount of oil-based solution can be 5 to 15 weight-% based on the matrix or the reservoir of the plaster ready for application.

The backing liner of the transdermal therapeutic system according to the present invention can be made of polyester, polypropylene, polyethylene or polyurethane, in each case optionally metallized, and the release lining can be made of polyester, polypropylene or coated paper.

For the matrix of the transdermal therapeutic system according to the present invention is contemplated a pressure adhesive or melt adhesive on the basis of polyacrylate, polyisobutylene, silicone, styrene-butadiene copolymer or styrene-isoprene copolymer, where for silicone Durotak(?) is particularly preferred.

The transdermal therapeutic system according to the present invention can be characterized by a semi-permeable membrane, in particular a membrane which controls the agent permeation.

The reservoir in the present transdermal therapeutic system can be formed by the backing liner or cover layer and the membrane or by a matrix. The membrane can be provided on the basis of silicone, polypropylene or polyvinyl acetate. The adhesive element according to the present transdermal therapeutic system can be provided in the form of a reservoir (when no membrane is provided) or in the form of a layer completely covering the membrane or only on its periphery. A pressure sensitive adhesive based on silicone can be used for the adhesive element.

DETAILED DESCRIPTION OF PREFERRED EMBODIMENTS

The invention will be described in more detail in the following in conjunction with the figures and examples.

Figure 1:
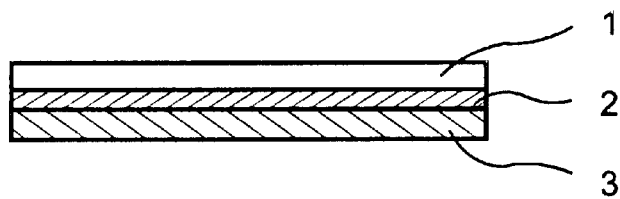
FIG. 1 shows a preferred embodiment of the present invention.

A matrix system is provided for example as shown in FIG. 1, where the active agent is dissolved in a self-adhesive matrix 2, which simultaneously accomplishes intensive contact with the skin and adhesion to the skin. The plaster comprises a backing liner 1 which is coated with the agent matrix 2. The backing liner 1 can be made of polyester (PETP), where alternative materials can be used including polypropylene, polyethylene or polyurethane of arbitrary thickness (for example 10 to 100 μm) and optionally metallized (for example with aluminum) and optionally printed. Furthermore, the plaster according to the invention is provided with a release liner 3, which is removed before use to then adhere the plaster onto the skin. The release liner 3 can be made of polyester (for example PETP) and can be transparent, opaque or printed. The release liner 3 can also be made of polypropylene or of coated paper, where any suitable thickness can be provided, for example 40 to 100 μm.

EXAMPLES 1 to 5

Five different plasters according to the invention were produced with the following characteristics.

Matrix: Durotak which is a PSA pressure adhesive for medical use based on polyacrylate.

Matrix surface weight: about 80 g/m²

Matrix thickness: 30 to 60 μm

Backing liner: polyester (PETP), namely Hostaphan RN 19

Release liner: polyester (PETP), namely Geiroflex PET 75 μl-s

D-α-tocopherol: free vitamin E concentrate from plant oils with the designation Copherol F-1300 (Henkel)

To produce the plaster, L-methadone base material was dissolved in about 160 mg acetone to produce a clear solution. In a closed mixing vessel, an amount of Durotak was prepared as can be taken from the following table. Thereafter, the tocopherol was added as well as the active agent solution and mixed for at least one hour.

The obtained solution was applied, for example with a doctor with automatic guidance, on the release liner at a thickness of 400 to 500 μm and dried for about one hour at about 50° C. Alternatively, the liner with applied agent matrix could be passed through three drying ovens with increasing temperature in the range of about 40 to 80° C.

After drying, the backing liner was laminated to the coated release liner. The obtained laminate was then cut into strips of 50 to 100 mm width. Individual plasters with a surface of 10 to 15 cm² were then stamped out of these strips. Each stamped-out plaster was then packaged in a four-sided closed envelope of aluminum/polyethylene laminate foil.

| Agent Concentration | Matrix Composition | |
|---|---|---|
| 3% L-methadone | L-methadone (base) | 2.4 mg |
| | D-α-tocopherol | 8.0 mg |
| | Durotak 326-1753 | 69.6 mg* |
| | | 80.0 mg |
| 5% L-methadone | L-methadone (base) | 4.0 mg |
| | D-α-tocopherol | 8.0 mg |
| | Durotak 326-1753 | 68.0 mg* |

-continued

| Agent Concentration | Matrix Composition | |
|---|---|---|
| 10% L-methadone | L-methadone (base) | 80.0 mg |
| | D-α-tocopherol | 8.0 mg |
| | Durotak 326-1753 | 8.0 mg |
| | | 64.0 mg* |
| 15% L-methadone | L-methadone (base) | 80.0 mg |
| | D-α-tocopherol | 12.0 mg |
| | Durotak 326-1753 | 8.0 mg |
| | | 60.0 mg* |
| 20% L-methadone | L-methadone (base) | 80.0 mg |
| | D-α-tocopherol | 16.0 mg |
| | Durotak 326-1753 | 8.0 mg |
| | | 56.0 mg* |
| | | 80.0 mg |

Dry mass, the adhesive was employed in the corresponding amount as a suspension in ethyl acetate with a solids content of about 40%.

Figure 2:
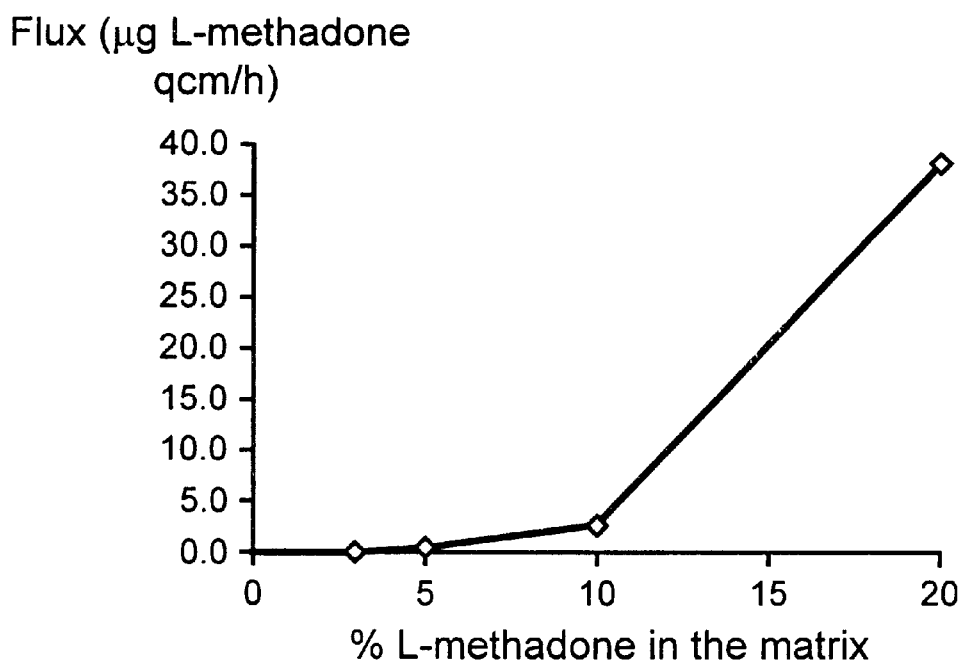
FIG. 2 shows a graphical representation of the relationship between flux and agent concentration in the matrix.

The obtained plasters, each with a permeation surface area of 2.5 cm$^2$ were then subjected two permeation tests in vitro. The respective plasters were applied to the isolated skin of female naked mice, from which the fat tissue under the skin had been removed. In a modified Franz diffusion cell, the time dependent permeation of the active agent into an acceptor medium was measured, namely a 0.9% sodium chloride solution. As one can derive from FIG. 2, it was surprisingly found that the amount of agent permeated through the mouse skin did not increase linearly with the increase in agent concentration but proportionally greater than linear.

I claim:

1. Transdermal therapeutic system (TTS) for the administration of methadone in the form of its racemate (D,L-methadone) or one of its enantiomers and/or of their pharmaceutically acceptable salts as the active agent for treating drug dependency or drug addiction comprising a self-adhesive layered matrix with an amount of an active agent or agents, and an additional amount of about 10% vitamin E or vitamin E derivative;

a backing liner provided on or over one side of the matrix; and a release liner provided on or over the other side of the matrix.

2. Transdermal therapeutic system according to claim 1, wherein the methadone is L-methadone.

3. Transdermal therapeutic system according to claim 1 wherein the amount of methadone comprises 5 weight-% to 20 weight-% based on the matrix.

4. Transdermal therapeutic system according to claim 1 wherein the methadone comprises 15 to 20 weight %.

5. Transdermal therapeutic system according to claim 1, wherein the matrix comprises an additional amount of vitamin E or vitamin E derivative, optionally in the form of an oil-base solution, such as D-α-tocopherol.

6. Transdermal therapeutic system according to claim 5 wherein the oil base solution is 5 to 10 weight % based on the matrix.

7. Transdermal therapeutic system according to claim 1, wherein said made of polyester, polypropylene, polyethylene or polyurethane, optionally metallized.

8. Transdermal therapeutic system according to claim 1, wherein said release liner made of polyester, polypropylene or coated paper.

9. Transdermal-therapeutic system according to claim 1 wherein the adhesive is selected from the consisting of polyacrylate, polyisobutylene, silicone, styrene-butadiene copolymer or styrene-isoprene copolymer.

10. Transdermal therapeutic system according to claim 9, wherein the matrix is a polyacrylate adhesive.

11. Transdermal therapeutic system according to clam 1, further comprising a semi-permeable membrane for controlling the active agent permeation.

12. Transdermal therapeutic system according to claim 11, wherein the membrane comprises of silicone, polypropylene or polyvinyl acetate.

* * * * *